United States Patent
Dropulic

(10) Patent No.: US 7,427,474 B2
(45) Date of Patent: Sep. 23, 2008

(54) HIGH-THROUGHPUT METHODS FOR IDENTIFYING GENE FUNCTION USING LENTIVIRAL VECTORS

(75) Inventor: Boro Dropulic, Ellicott City, MD (US)

(73) Assignee: VIRxSYS Corporation, Gaithersburg, MD (US)

( * ) Notice: Subject to any disclaimer, the term of this patent is extended or adjusted under 35 U.S.C. 154(b) by 0 days.

(21) Appl. No.: 10/627,940

(22) Filed: Jul. 25, 2003

(65) Prior Publication Data

US 2004/0203017 A1    Oct. 14, 2004

Related U.S. Application Data

(63) Continuation-in-part of application No. PCT/US02/02287, filed on Jan. 25, 2002.

(60) Provisional application No. 60/264,272, filed on Jan. 25, 2001.

(51) Int. Cl.
*C12Q 1/68* (2006.01)
*C12N 15/86* (2006.01)

(52) U.S. Cl. ........................................ 435/6; 435/320.1

(58) Field of Classification Search .................. None
See application file for complete search history.

(56) References Cited

U.S. PATENT DOCUMENTS

| | | | |
|---|---|---|---|
| 5,814,500 A | 9/1998 | Dietz | 435/172.3 |
| 5,817,491 A * | 10/1998 | Yee et al. | 435/456 |
| 6,372,965 B1 * | 4/2002 | Lightner et al. | 800/298 |
| 6,627,442 B1 | 9/2003 | Humeau et al. | |
| 6,830,892 B2 | 12/2004 | Marasco et al. | |

| | | | |
|---|---|---|---|
| 2004/0018570 A1 * | 1/2004 | Sedivy et al. | 435/7.23 |

FOREIGN PATENT DOCUMENTS

| | | |
|---|---|---|
| EP | 1022335 | 7/2000 |
| WO | WO99/24563 | 5/1999 |
| WO | WO99/36516 | 7/1999 |
| WO | WO-99/41397 | 8/1999 |
| WO | WO-99/64582 | 12/1999 |
| WO | WO00/01846 | 1/2000 |
| WO | WO00/24912 | 5/2000 |
| WO | WO-02/24897 | 3/2002 |

OTHER PUBLICATIONS

Sedivy et al., J. Clin. Invest. 103 (8) 1179-1190, 1999.*
Budde et al. Oncogene, 1998, 19, 1119-1124.*
Dennery et al., J. Biol Chem., 272, 23, 14937-14942, 1997.*
Tovar et al., Nucl. Acids Res. 24 (15), 2942-2949, 1996.*
Bigbee et al. Brain Research 861, 354-362, 2000.*
Fire et al., TIGS, 1999, 15, 9, 358-363.*
Buckler, et al. (1991) *Proceedinsg of National Academy of Science* 88:4005-4009.
Morgan et al. (1992) *Nucleic Acids Research* 20:5173-5179.
Dropulic et al., PNAS USA (1996) 93:11103-11108.
Mautino et al., Human Gene Therapy (2000) 11(14):2025-2037.
Mautino et al., Gene Therapy (2000) 7(16):1421-1424.
Mautino et al., Human Gene Therapy (2000) 11(6):895-908.
Japanese Office Action for Application No. 2002-559860, date mailed on Nov. 20, 2007, 5 pages.

* cited by examiner

*Primary Examiner*—Nancy Vogel
(74) *Attorney, Agent, or Firm*—Morrison & Foerster LLP

(57) ABSTRACT

The present invention relates to methods and compositions for the efficient identification of one or more functionalities of a product encoded by a nucleic acid sequence of interest. The methods utilize the abilities to over and/or under express the product in a cell, as well as the combination of these results, to permit the identification of at least one of the product's cellular or in vivo functionality.

35 Claims, 1 Drawing Sheet

RNA expression (in relative units)

| encoded gene product | Con. | Seq 1 | | | Seq 2 | | | Seq 3 | | | Seq 4 | | |
|---|---|---|---|---|---|---|---|---|---|---|---|---|---|
| | | O | U | C | O | U | C | O | U | C | O | U | C |
| transcription factor 1 | 100 | 100 | 100 | 0 | 100 | 100 | 0 | 100 | 100 | 0 | 100 | 100 | 0 |
| transcription factor 2 | 100 | 30 | 200 | 0/170 | 100 | 100 | 0 | 100 | 100 | 0 | 100 | 300 | 0/200 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| transcription repressor 1 | 100 | 30 | 200 | 0/170 | 100 | 100 | 0 | 100 | 100 | 0 | 100 | 100 | 0 |
| transcription repressor 2 | 100 | 200 | 30 | 170/0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| kinase 1 | 100 | 100 | 100 | 0 | 100 | 100 | 0 | 100 | 100 | 0 | 100 | 100 | 0 |
| kinase 2 | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| structural protein 1 | 100 | 100 | 100 | 0 | 300 | 90 | 210/0 | 100 | 100 | 0 | 100 | 100 | 0 |
| structural protein 2 | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| oxidoreductase 1 | 100 | 100 | 100 | 0 | 100 | 100 | 0 | 20 | 105 | 0/85 | 20 | 105 | 0/85 |
| oxidoreductase 2 | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| receptor 1 | 100 | 100 | 100 | 0 | 100 | 100 | 0 | 20 | 105 | 0/85 | 20 | 105 | 0/85 |
| receptor 2 | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| secreted protein 1 | 100 | 100 | 100 | 0 | 100 | 100 | 0 | 20 | 105 | 0/85 | 20 | 105 | 0/85 |
| secreted protein 2 | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| all known sequences | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| etc... | 100 | 100 | 100 | 0 | 100 | 100 | 0 | 100 | 100 | 0 | 100 | 100 | 0 |
| unknown sequences (e.g. Seq 1) | 100 | 300 | 0 | 300/0 | 100 | 100 | 0 | 100 | 100 | 0 | 100 | 100 | 0 |
| Seq 2 | 100 | 100 | 100 | 0 | 300 | 0 | 300/0 | 100 | 100 | 0 | 100 | 100 | 0 |
| Seq 3 | 100 | 100 | 100 | 0 | 300 | 90 | 210/0 | 300 | 0 | 300/0 | 100 | 100 | 0 |
| Seq 4 | 100 | 100 | 100 | 0 | 100 | 100 | 0 | 100 | 100 | 0 | 150 | 50 | 100/50 |
| etc... | 100 | 100 | 100 | 0 | 100 | 100 | 0 | 100 | 100 | 0 | 100 | 100 | 0 |

"Con" = control cell expression
"O" = overexpression
"U" = underexpression
"C" = combined effect

Figure 1

HIGH-THROUGHPUT METHODS FOR IDENTIFYING GENE FUNCTION USING LENTIVIRAL VECTORS

RELATED APPLICATIONS

This application is a continuation-in-part ("CIP") of PCT/US02/02287, filed Jan. 25, 2002 and designating the United States, which claims benefit of priority to U.S. Provisional Patent Application 60/264,272, filed Jan. 25, 2001, both of which are hereby incorporated by reference in their entireties as if fully set forth.

TECHNICAL FIELD

The present invention is directed to methods, as well as compositions related thereto, for the efficient identification of one or more functionalities of a product encoded by a nucleic acid sequence. The methods utilize the abilities to over and/or under express the product in a cell, as well as the combination of these results, to permit the identification of at least one of the product's cellular or in vivo functionality.

BACKGROUND ART

The tremendous efforts at sequencing the genomes of human beings and other organisms has produced a vast amount of nucleic acid and protein sequence information for additional analysis. Much of the sequence information is now, or will be, the subject of both biochemical and functional characterization. The sequence information also serves as the raw material for "bioinformatics", where the sequence itself is used in comparisons with other sequences for which the structure, function, or other characteristics have been previously identified. The great hope and expectation for these efforts is that with the identification of functionalities encoded by genetic sequences, additional therapeutic products and treatments can be developed for diseases in humans and other organisms.

The effort to identify functions encoded by genetic sequences has focussed, at least initially, on sequences that encode actual gene products, or "genes". Earlier approaches sought to clone and sequence only genes based on tools and strategies for using positional cloning to map and clone genes. While labor intensive, positional cloning has been successful in locating genes associated with various diseases. Initially, genetic mapping is performed based on large families of related individuals to locate a disease associate gene at the level of chromosomal location and in the range of centimorgans. Next, and with a significant increase in effort, the work becomes one of physically mapping the genes so that centimorgans are reduced to megabasepairs and then finally to particular nucleotides. Examples of successes with positional cloning include the identification of genes associated with cystic fibrosis and Huntington's disease.

Other approaches to the isolation of genes include exon trapping (Buckler et al. (1991) P.N.A.S. 88:4005-4009) and direct selection (Morgan et al. (1992) N.A.R. 20:5173-5179). These methods identify potential genes in large genomic regions which are then sequenced and used in confirming the genes as actually expressed. In some cases, cells that normally express the potential gene are unknown, and it remains necessary to confirm the expression of the genes and identify the functionality of the encoded product.

An initial advantage available with positional cloning over the above two methods is that there is no need for knowledge concerning the functional or physiological role of the gene product of the identified gene. The identification is made based on following a phenotypic trait followed by studying genetic segregation of a particular sequence with the trait. But after identification, there may still be difficulties in determining the functional role of the gene product for the design of appropriate therapies. Without knowing the functional role of the encoded product, it remains difficult, for example, to identify suitable agents to use as pharmaceuticals to appropriately target the gene product. Additionally, it remains unknown how the identified gene is involved in the progression from onset and progression to the later stages of the disease.

A more recent approach to the isolation of genes has been based on massive sequencing efforts designed to identify all expressed sequences in a genome. Completion of such efforts in the human and *Drosophila* genomes, as well as some microorganisms, have been recently reported. But with the production of such large amounts of sequence information, the need for a rapid and efficient means for identifying the functionality of encoded gene products increases further. This need has led to intensive commercial and industrial activity for additional methods to identify gene function.

One means for identifying function is through bioinformatics, which seeks to determine functionality based on similarities between a new sequence and other sequences for which the structure, function, or other characteristics have been previously identified. Bioinformatics is most often performed with computer programs and thus have been termed to occur "in silico". One drawback of bioinformatics, however, is that it only provides a starting point for possibly validating a postulated functionality of a gene sequence. Until a new sequence is actually expressed and characterized within a living cell or organism, the supposed functionality remains a hypothesis to be proven.

An approach to validate an assigned gene function is via the use of small animal models. For example, transgenic mice have been used for the overexpression of gene sequences in attempts to identify the encoded functionality. Gene sequences have also been used in the production of "knock-out" mice where the endogenous mouse sequence is no longer expressed. But the time and cost of transgenic approaches have limited their usefulness to studies of only a few sequences at a time.

Another approach has been to make use of cell cultures to overexpress a gene sequence of interest. Unfortunately, there is no rapid and efficient means for reliably producing a "knockout" cell where the endogenous cellular sequence is not expressed or overexpressed. Overexpression methods are, however, limited by the vector system used to deliver and express the gene. As an initial matter, known vector systems limit the number of cells that are transfected with the gene. For example, plasmid vectors have low transfection efficiencies and thus require the use of a selectable marker to isolate transfected cells. But the expression of a marker gene from the plasmid vector tends to skew the phenotype detected because the gene of interest is not the only gene being overexpressed in the cell. Stated differently, expression of the gene of interest is not the only initial perturbation occurring in the cell. As such, the determination of gene function may be significantly mistaken due to skewing by expression of the marker gene. The same selectable marker mediated skewing is seen with some viral vectors, such as onco-retroviral vectors.

Higher transfection efficiencies are available from other viral vectors, such as adenovirus based vectors, but these vectors often fail to provide stable expression of the gene of interest. More importantly, such vectors often have large numbers of their own genes to express or suffer the risk of contamination due to co-infection by helper virus. The expression of vector and/or helper virus genes again perturbs the intracellular environment and skews the detected phenotype and thus affects the determination of gene function.

An additional limitation on the use of vector based overexpression is found with the uncertainty as to what resultant phenotype should be, or can be, detected in the transfected cell. Moreover, such methods rarely use primary cells but instead use cell lines or diseased cells where any identified gene function remains suspect because of the abnormal cellular environment.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention provides compositions and methods to increase the ability to identify one or more functions of products encoded by unidentified gene sequences or to further identify or confirm one or more functions of known gene sequences. Therefore, and in one aspect, the invention provides a lentiviral vector capable of high transduction in primary cells, preferably without altering the overall gene expression profile of the cell, except for the expression of a specific payload encoding, or targeted to, one or more gene sequences under investigation. Gene expression profile refers to the levels of expression, at the RNA and/or protein levels, of coding sequences in a cell.

The present invention thus provides a clear validating system for the determination of gene function, where the cellular effects of overexpression may be compared to and correlated with those of inhibition. The invention may be applied, as a non-limiting, but important example of a large scale gene chip experiment where the background level(s) of gene expression is a significant difficulty to data interpretation. The (cellular or endogenous) genes identified or confirmed to be affected by increased and/or decreased expression of a gene sequence of interest can be placed in a matrix for analysis to describe the function of the gene under investigation.

The present invention provides for the determination of one or more functionalities of a given unidentified or known gene sequence of interest by at least two means. First, the gene sequence, or one or more portions thereof, is inserted in a vector and introduced into a cell for expression of the encoded gene product. The level of expression can of course be attenuated, but preferably, the sequence is overexpressed. After expression occurs, changes in the expression, composition, or form of endogenous cellular factors, in comparison to normal cells without said vector, are detected and analyzed. This permits the identification of what cellular factors are affected by the sequence being expressed or overexpressed. Without limiting the scope of the invention, the actual effect on the cellular factor may include that of changes in its level of expression (e.g. at the protein and/or RNA levels), changes in its amino acid composition (e.g. number and type of subunits and/or splice variants), and changes in its state of post-translational modification (e.g. phosphorylation and/or glycosylation and/or lipid modification) or location (e.g. subcellular location as well as being soluble, membrane associated, or by insertion of at least one portion of the factor into the hydrophobic portion of a membrane). Cellular factors include those with one or more identified function as well as those for which a function has yet to be identified.

Second, expression of the unidentified or known gene sequence is inhibited or terminated in a cell. Without limiting the scope of the invention, the inhibition may be by use of all or part of the gene sequence to recombine with the endogenous copy or copies of the sequence in said cell to terminate its expression. Alternatively, the gene sequence, or one or more portions thereof, maybe inserted in an antisense orientation in a vector. The expression of the sequence, or portion thereof, may be regulated such that it is expressed only when desired to produce an antisense nucleic acid.

Preferably, the antisense sequence is ligated to co-localization sequences capable, upon expression with the antisense sequence, of co-localizing the antisense sequence with the complementary endogenous cellular, and "sense", sequence. In some embodiments of the invention, the antisense sequence is used to target a ribozyme to cleave the endogenous mRNA. The vector is introduced into a cell for expression of the antisense sequence, which then binds to and results in the inhibition of expression of the complementary endogenous cellular sequence.

Alternatively, polynucleotides corresponding or complementary to all or part of a gene sequence of interest may be used in the design or testing or use of polynucleotides for post-transcriptional gene silencing (PTGS). PTGS is mediated by the presence of a homologous double stranded RNA (dsRNA) which leads to the rapid degradation of RNAs encoding a targeted gene product. One form of PTGS is RNA interference (RNAi) mediated by the directed introduction of dsRNA. Another form is via the use of small interfering RNAs (siRNAs) of less than about 30 nucleotides in double or single stranded form that induce PTGS in cells. A single stranded siRNA is believed to be part of an RNA-induced silencing complex (RISC) to guide the complex to a homologous MRNA target for cleavage and degradation. siRNAs induce a pathway of gene-specific degradation of target mRNA transcripts. siRNAs may be expressed in via the use of a dual expression cassette encoding complementary strands of RNA, or as a hairpin molecule.

Therefore, the invention also provides for methods of inhibition or termination of expression of a gene sequence by the use of short interfering (si) RNAs or ribozymes targeted against said sequences. The use of ribozymes to inhibit gene expression and virus replication is described in U.S. Pat. No. 6,410,257 via use of a conditionally replicating vector for other purposes.

After expression of the antisense, ribozyme, or siRNA sequence(s) to inhibit expression of the complementary cellular sequence, changes in the expression, composition, or form of cellular factors as described above, in comparison to untreated normal cells, are detected and analyzed. This permits the identification of what cellular factors are affected by decreasing or suppressing expression of the endogenous cellular sequence corresponding to the gene of interest (complementary to the antisense sequence used).

Preferably, the above over and underexpression of a gene sequence of interest is conducted by use of a viral vector capable of high efficiency transduction without significant expression of endogenous vector gene sequences or helper virus contamination. Examples of such vectors include those described in pending U.S. patent application Ser. No. 09/667,893 entitled "Improved Conditionally Replicating Vectors, Methods for Their Production and Use", filed Sep. 22, 2000, which is hereby incorporated by reference as if fully set forth. Even more preferred are embodiments of the invention wherein the transduced cells are primary cells.

Optionally, the above vectors for over and underexpression are integrated into the cellular genome as part of the transduction process.

Alternatively, the vectors of the invention, such as a lentiviral vector, may be used to introduce more than 1) a single inhibitory or terminating sequence, 2) an overexpressed gene sequence, or 3) a combination of the two. Nucleic acid constructs for the expression of such multiple sequences may contain a separation of the gene sequences by transcriptional pause elements, stop elements, by a (native) cis-acting ribozyme that self cleaves the transcript between the two encoded RNAs, or by a combination of these elements. Alternatively, dual vectors may be used to target the same cell in order to allow simultaneous gene knockdown, expression, or a combination of knockdown and expression.

In a preferred form of the invention, changes in the expression of cellular factors are detected. Additionally, the detected changes in expression of cellular factors from the two approaches can be combined and compared to provide additional information on one or more functions of the unidentified or known gene sequence under study. The combination of the detected changes in expression of cellular factors is similar to "subtraction" techniques used to study the differential expression of cellular factors upon a perturbation in cellular conditions, such as before or after a temperature shift or the addition of a growth factor.

Detailed analysis of the results from overexpressing, underexpressing and the results from both permits the identification of one or more gene functions of a sequence of interest based on a reliable intracellular environment initially perturbed only by changes due to over or under expressing the gene sequence of interest. A function of said gene sequence of interest is thus identified based on the identity of, or effects on, one or more cellular factors affected by changes in the expression of said sequence. Non-limiting examples of possible functions include regulating the expression of said one or more factors and affecting the activities of said one or more factors.

The analysis also permits the identification of one or more cellular factors that are functionally related to the sequence of interest. One such group of cellular factors would exhibit increased expression upon over expression of the sequence of interest and exhibit decreased expression upon inhibition of expression of the sequence of interest. Another group of cellular factors would be the inverse of the above, exhibiting decreased expression upon over expression of the sequence of interest and exhibiting increased expression upon inhibition of expression of the sequence of interest.

The groups of cellular factors that are thus identified may be viewed as part of a "coordinated response" to perturbations in the expression of the sequence of interest. The "coordinated response" may be that of a single regulatory, biochemical or metabolic pathway or other functionality of a cell. It also provides a means for the identification of functional relationships between cellular factors and the product of the gene sequence of interest.

The ability to identify "coordinated response" cellular factors by observing the effects of both over and underexpression of a sequence of interest provides an advantageous means of decreasing or eliminating time spent on evaluating or considering cellular factors that display a change in expression only upon either the over expression, or under expression, of a sequence of interest. Such "coordinated response" cellular factors may be readily classified as a separate group for separate study, consideration, and/or analysis. The present invention improves the ability to quickly and efficiently identify functionalities of the gene sequence of interest since it decreases the expense in time and money spent on simultaneously relating all the effects of perturbing the expression of the sequence of interest. The invention provides a means to focus only on those effects that are correlated with both the over and under expression of the gene sequence of interest.

The invention may be practiced by detecting changes in one or more cellular factors of a cell or cell type in which the gene sequence of interest has already been found to be expressed. A non-limiting example of such a gene sequence of interest is in the case of an open reading frame which is found to be expressed in certain cell types or under certain disease conditions. Alternatively, the invention may be practiced by detecting changes in a cell or cell type in which the gene sequence of interest has not been detected as expressed. Preferably, the cells or cell types are human cells, although any animal, plant or microorganism cell may also be used. Methods for the introduction of a gene sequence of interest into a cell are discussed below.

The present invention thus provides analytical methods, compositions and systems comprising two or more vectors for the identification of one or more functionalities of a gene sequence of interest. Optionally, at least a third vector is used to over or under express yet another gene sequence to provide further information on one or more functionalities of a gene sequence of interest.

In another aspect of the invention, a high throughput, and optionally computerized or robot implemented, system for identifying gene function is provided. In such embodiments, the invention provides libraries of vectors and transduced cells arranged in a multiplicity of compartments. With respect to vectors, the libraries contain compartments containing either a vector for overexpressing a gene of interest or a vector for underexpressing a gene of interest. Such vector libraries may be very efficiently used to transduce cells to produce a library of cells in a multiplicity of compartments, each of which contains cells transduced with one vector. The vector libraries may optionally be propagated in packaging cells prior to their use in cell transduction.

The libraries of transduced cells may be analyzed for the effects of over or under expressing a gene sequence of interest by use of machine implemented microarray or macroarray technologies known in the art. An example of which is "gene chip" technology whereby gene expression of a large number of sequences may be determined via a single "chip" used for the hybridization of mRNA, or the corresponding cDNA, isolated from cells. The invention includes a composition of matter that is an array for the practice of the disclosed methods, optionally in contact with material from cells that are over and/or under expressing one or more gene sequence of interest (e.g. in contact with RNA, protein, other cellular material, or extracellular material from such cells).

The libraries of transduced cells may also be subject to further treatment or changing conditions before analysis of effects on cellular factors. The cells, and hence effects on cellular factors, may also be analyzed temporally. The function of a gene sequence may also be assessed through cellular differentiation and function in vivo in culture, or after transplantation in an animal model, or in human or non-human primates.

A variety of methods may be used to detect changes in cellular factors. Such methods include the determination of messenger RNA levels, protein expression levels, protein activity levels, effects on protein phosphorylation, effects on protein or nucleic acid processing, effects on RNA stability, effects on signal transduction or second messengers, and so forth.

The invention also provides methods for altering the expression, composition, or form of one or more cellular factors in a cell by over expressing, inhibiting the expression of, or simultaneously inhibiting and overexpressing a gene sequence or sequences for which a function has been identified by the methods described above. Such methods may also be used to alter the phenotype of said cell.

The invention provides numerous advantages beyond the ability to identify one or more functions of encoded gene products for which no activity is known. These include the ability to provide additional information on the function of gene products for which some activity information is already known; the ability to provide information on the effect of over or under expressing one functionless gene product on the expression of another functionless gene product; and the ability to conduct the same analysis on different cell types which express different endogenous sequences.

The invention also provides a means for increasing the expression of known gene products. Once a gene sequence of interest has been found to increase expression of a desirable and known cellular gene product, the gene sequence of interest may be used at least to increase expression of the product for subsequent isolation or purification.

It is a further advantage of the present invention that there is no requirement for knowledge or speculation on the functionality of the gene of interest. In embodiments of the invention where there is knowledge concerning the functionality of the gene of interest, the present invention advantageously provides means to identify one or more other functionalities that may have been previously unknown and/or to confirm one or more other functionalities that may have been previously known or suspected. The latter is of particular relevance with respect to a disease associated gene sequence of interest which can be used in combination with the present invention to identify or confirm one or more other functionalities of the sequence. For example, and without limiting the invention, a decrease in the level of a product encoded by a disease associated gene sequence may have been identified as a useful pharmacological treatment for the disease. But a decrease in the expression level of the sequence may be suspected of causing a compensatory increase in another cellular factor which would decrease the efficacy of the treatment. Use of the disease associated gene sequence in the present invention provides an advantageous means of determining whether such a compensatory increase occurs as well as the identity of the compensatory cellular factor. This factor is a second target which may be simultaneously decreased to improve the treatment of the disease.

Yet another advantage of the invention is that relatedness based on gene functionality may be determined and used to produce a map of functional relationships.

BRIEF DESCRIPTION OF THE FIGURES

FIG. 1 shows sample results when various sequences of interest, "Seq" 1 to 4, are over or under expressed. The effects on the expression of various cellular gene sequences are depicted along with the level of expression in control cells indicated as "100" in arbitrary relative units. In this figure, "Seq" 1-4 may represent sequences that are unidentified, putatively identified and/or known. The results may be increased at will based upon inclusion of more cellular gene sequences for evaluation (more rows added) or more sequences of interest to over and under express (more columns added).

MODES OF CARVING OUT THE INVENTION

The present invention provides methods and compositions for the identification of one or more functionalities of the gene product of a given sequence. Preferably, the sequence is human, but one or more non-human sequences may also be used in combination with the present invention to identify their effect(s) on cellular factors in human cells. Advantageously, there is no prerequisite for knowledge regarding the encoded functionality. If the functionality is known, however, the present invention permits the confirmation of said functionality as well as the possible identification of previously unknown or unappreciated functionalities.

In a preferred embodiment, the invention provides a vector for overexpressing a given unidentified or known gene sequence in a cell. Such expression is preferably under tight and/or inducible regulatory control. An "unidentified" sequence is considered to not yet have confirmation of a cellular or biochemical functionality. A "known" sequence is considered to have been confirmed as having one or more cellular or biochemical functionalities. Preferably, the overexpression occurs without simultaneous expression of other vector borne sequences, such as, but not limited to, selectable markers. Thus the intracellular environment is affected only by the overexpression of the sequence of interest and the effects of said overexpression more accurately reflect one or more functionalities of said sequence.

Cells transduced according to this embodiment of the invention are analyzed for cellular factors, defined herein as any cellular gene product (e.g. proteins or RNA) or metabolite thereof (e.g. molecules such as sugars and lipids), that are affected by overexpression of said gene sequence. The effects of overexpression are in comparison to normal cells not overexpressing said sequence. Preferably, normal cells are mock transfected with the vector but without expression of said gene sequence. By way of example, and without limiting the invention, overexpression of a given gene sequence (such as that encoding an inducer of cellular differentiation) would increase expression of RNAs encoding one or more cellular factors (such as those encoded by genes involved in differentiation or the differentiated state) in comparison to normal cells. Alternatively, overexpression of some gene sequences (such as a transcriptional repressor) would result in decreased expression of one or more cellular factors. Lastly, some cellular factors are unaffected by overexpression of some gene sequences. The invention includes the ability to identify one or more functions of gene sequences of interest that encode modulators of one or more cellular factors by binding to nucleic acids encoding, or regulating the expression of, said factor(s).

In another embodiment, the invention provides a vector for inhibiting, suppressing or otherwise decreasing the expression of an unidentified or known gene sequence in a cell. This again preferably occurs in the absence of expression of other vector borne sequences, such as, but not limited to, selectable markers. The intracellular environment is thus again only affected by the complete or partial underexpression of said sequence, and the effects more accurately reflect one or more functionalities of said sequence. While this underexpression of a gene sequence appears to require that the cells normally express the sequence endogenously, the present invention may still be practiced with cells that do not express the sequence because there would simply be no significant difference between the cells transduced with vector to effect underexpression and mock transduced cells. Alternatively, cells that normally express the sequence endogenously, and thus are capable of underexpressing it, may be first identified by well known and standard methods in the art such as a Northern blot using all or part of the sequence as a probe. To identify such cells rapidly, a "tissue blot", wherein RNA from a variety of cell types is prepared and simultaneously subjected to Northern blotting, may be used.

To underexpress the unidentified or known gene sequence, but without limiting the invention, it may be inserted in an antisense orientation in a vector for transduction and expression in a cell. Such expression is preferably under tight and/or inducible regulatory control. The insertion of the entire sequence in antisense orientation is of course not necessary and one or more portions of the unidentified or known sequence may be used. Preferably, the antisense sequence is operably linked to co-localization sequences which, upon expression with the antisense sequence, of co-localizing the antisense sequence to be tracked to the same cellular locations as the complementary endogenous cellular, or "sense", sequence. While the antisense sequence can be used directly to result in the non-expression of the endogenous mRNA, the antisense sequence can also be part of the targeting sequence to direct a ribozyme to cleave the endogenous RNA. In such embodiments, the vector is of course designed to be able of expressing the antisense sequence as an operative part of an encoded ribozyme to target the endogenous sequence. The vector is then introduced into a cell for expression of the antisense sequence, which then binds to and results in the inhibition of expression of the complementary endogenous cellular sequence.

A variety of antisense sequences derived from various portions of the gene sequence to be suppressed may be used initially to determine which is most suitable for decreasing the expression of a cellular sequence. In one embodiment of the invention, and for the most complete suppression of endogenous cellular expression, the antisense sequence should be directed to a conserved portion of the endogenously expressed sequence in case the cell is heterozygous for the gene sequence being suppressed. Of course multiple antisense sequences may also be used. Alternatively, the gene sequence of interest may be used to prepare vectors that would recombine with the endogenous copies of the gene sequence of While a variety of co-localization sequences may be used to co-localize the antisense molecule to the endogenous RNA, preferred sequences are the U1, U2, U3, U4, U5 or U6 snRNA, all of which may be operably linked to the above described antisense or ribozyme sequences. More preferably, the co-localization sequence used is a U1 snRNA/promoter cassette as described in Dietz (U.S. Pat. No. 5,814,500), which is hereby incorporated by reference in its entirety as if fully set forth.

While for many gene sequences, the ability to suppress its expression entirely provides the clearest information on the results of its underexpression, it should be noted that the ability to suppress, partially or entirely, the expression of a sequence is an aspect of the present invention. Partial suppression of gene expression is of particular advantage when the gene sequence encodes a product critical for cell viability. Such gene sequences may be readily identified by the lethal effect on a cell upon complete or nearly complete suppression of expression. A non-limiting example of how to achieve partial suppression is to target only one endogenously expressed sequence in a cell that is heterozygous for said sequence.

Cells transduced according to this embodiment of the invention are analyzed for cellular factors that are affected by underexpression of said gene sequence in comparison to normal cells expressing said sequence. The normal cells are again preferably mock transfected with the vector but without causing underexpression of said gene sequence. By way of example, and without limiting the invention, underexpression of a given gene sequence (such as that encoding a transcriptional repressor) would increase expression of RNAs encoding one or more cellular factors (such as those encoded by genes repressed by said repressor) in comparison to normal cells. Alternatively, underexpression of some gene sequences (such as transcriptional activators) would result in decreased expression of one or more cellular factors. Lastly, some cellular factors are unaffected by underexpression of some gene sequences.

While not absolutely necessary for the practice of the invention, vectors for over or under expressing sequences in accord with the present invention are preferably capable of high efficiency and stable transduction of cells of up to 100% efficiency. Alternatively, they are maintained episomally, preferably at high copy number although the invention may also be practiced with low copy number episomal constructs. Stable integration may be enhanced by stimulating the cells being transduced with an appropriate ligand followed by culturing the cells under standard conditions (see co-pending U.S. application Ser. No. 09/653,088 filed Aug. 31, 2000 and titled METHODS FOR STABLE TRANSDUCTION OF CELLS WITH VIRAL VECTORS, and allowed in June 2003) which is hereby incorporated in its entirety as if fully set forth. Such vectors are also preferably designed to express little or no vector borne sequences other than the gene of interest, whether in sense or antisense orientation. In some embodiments of the invention, the vectors further contain sequences sufficient to permit integration of the vector into the cellular genome. Such recombination events may be based on homologous recombination or integrase mediated events due to enabling sequences present on the vector. As a non-limiting example, when a Lentiviral derived vector is used, the normal Lentiviral integration sequences can facilitate stable integration into the host cell genome. Such Lentiviral vectors are preferably pseudotyped by use of a heterologous viral envelope (env) protein, such as, but not limited to, that of a retrovirus. More preferably the env protein is an HIV-1, HIV-2, or MMLV envelope protein; the G protein from Vesicular Stomatitis Virus (VSV), Mokola virus, or rabies virus; GaLV, Alphavirus E1/2 glycoprotein, or RD1114, an env protein from feline endogenous virus. Alternatively, sequences encoding a chimeric envelope protein may also be used. Sequences encoding an envelope protein from the following viral families may also be used: Piconaviridae, Tongaviridae, Coronaviridae, Rhabdoviridae, paramyxoviridar, Orthomixoviridae, Bunyaviridae, Arenaviridae, Paroviridae, Poxviridae, hepadnaviridae, and herpes viruses.

The given unidentified or known gene sequence to be over or under expressed can be from any source and may even be partially identified. Non-limiting examples of unidentified or partially identified sequences include those obtained from the isolation and characterization of EST (expressed sequence tag) sequences and any nucleic acid sequence considered to possibly encode a gene product, whether RNA or proteinaceous in form. Such sequences include those identified by the assembly of EST sequences or otherwise determined to encode a gene product. These sequences include those that have undergone bioinformatics analysis and thus have homology to other known or uncharacterized sequences. By way of example, and without limiting the invention, a sequence encoding an open reading frame for which no function is assignable may be used in the present invention to identify one or more of its functions in a cell. Similarly, a sequence encoding an open reading frame with homology to a DNA binding protein (based on bioinformatics analysis, for example) may be used in the present invention to confirm its putative functionality as a transcription factor.

Non-limiting examples of known sequences may be from any source and include those for which one or more functionalities have been assigned. Such sequences include those in publicly available databases as well as any sequence for which the encoded gene product has been characterized. Such sequences may nevertheless be used in the present invention to confirm known functionalities and/or identify additional functionalities. By way of example, and without limiting the invention, a sequence encoding a kinase identified solely as phosphorylating a cytoplasmic protein may be found to cause elevated expression of a nuclear transcription factor upon overexpression of the kinase. Without being bound by theory, the kinase may directly or directly result in the increased expression of a transcription factor via its kinase activity. One possibility would be where the kinase phosphorylates the transcription factor to inactivate it, thereby causing an increase in its expression via a feedback loop. Other effects on cellular factors as described herein may also occur via one or more feedback loops.

Additionally, artificial sequences, such as recombinant fusion or other chimeric constructs as well as mutated versions of the sequences discussed above, may also be used in the present invention to identify their function(s). This aspect of the invention may be of particular advantage in the confirmation of a particular artificial protein or mutagenized protein as capable of substituting for the function(s) of a wildtype protein. For example, and without limiting the invention, a synthetic mutant version of the p53 protein which is able to multimerize with itself but not with dominant negative mutant forms of p53 may be used in the present invention to confirm its ability to substitute for wildtype functional p53. With such confirmation, the synthetic mutant may be used in therapeutic contexts to treat cells containing the dominant negative p53 mutation.

The introduction of unidentified or known sequences into the vectors for the practice of the invention may be by any means. Preferably, it is performed by highly efficient means that may be performed in parallel and minimize the need for multiple cloning steps or the need for confirmation of cloning steps. More preferably, the insertion of sequences into vectors is performed by automated techniques. As a non-limiting example, the gene sequence of interest may be first cloned into an initial vector capable of allowing the sequence to be subsequently introduced into the over and under expression vectors of the invention. This may be by the use of a recombination mediated insertion system such as the Gateway™ cloning system from Life Technologies, which utilizes att sites in the plasmids to permit highly efficient transfer of sequences between vectors. Thus in one embodiment of the invention, the vectors for over and under expressing a gene sequence may contain appropriate att sites to permit efficient insertion of gene sequences.

In an automated embodiment, the insertion of gene sequences may be based upon the use of arrays containing a library of gene sequences. Such sequence containing arrays may be used to generate a plurality of additional arrays, organized based upon the first library containing the gene sequences. This plurality of arrays may sequentially include one or more of the following: an array that contains the gene sequences modified with appropriate linkers; an array that contains the modified gene sequences for amplification; an array that contains the modified sequences introduced into an initial vector for propagation or further cloning; an array of the sequences transferred from the initial vector to one or more vectors of the invention; and an array of such vectors appropriately packaged prior to their use to transduce cells.

One advantage provided by the use of such arrays is the ability to continue to use the organization present in such arrays when over and under expressing a library of gene sequences according to the invention. For example, the array arrangement containing the library of packaged vectors can be used to transduce an array of cells, which can then be harvested, partially or completely, to analyze the effects of over and under expression of the gene sequences of the array on cellular factors.

Cells for use in the present invention may be any kind of cell. But for optimal determination of function, the cell should be from the same organism as the gene sequence to be over or under expressed. Sequences may nevertheless be heterologous to the cells in which they are express to determine their function(s) in the cell. Preferably, the cells are human, and the gene sequence of interest is studied at least initially in cells from which the sequence has been found to be expressed. By way of a non-limiting example, a fungal sequence may be expressed in mammalian cells to determine its function(s) therein. This aspect of the invention is of particular advantage if the counterpart mammalian sequence to the fungal sequence is known. This permits a comparison to the effects of underexpressing the mammalian sequence to confirm the fungal sequence as capable of functioning as a substitute for the mammalian sequence. If so, the fungal sequence may encode a product which may be a therapeutic substitute for the product encoded by the mammalian sequence.

Preferred cell types for the practice of the invention are eukaryotic cells, more preferred are primary eukaryotic cells, and most preferred are primary mammalian cells and human cells. Preferred cells are those of human tissues, including, but not limited to, neuronal cells, brain cells, epithelial cells, connective tissue cells (e.g. fibroblasts, osteoblasts, and adipose cells), blood cells (e.g. leukocytes, lymphocytes, monocytes and neutrophils), sensory cells, muscle cells, sensory cells (e.g. ocular cells and hair cells), lung cells, heart cells, liver cells, skin cells, pancreatic cells, breast cells, kidney cells, intestinal cells, stomach cells, colon cells, prostate cells, ovarian cells, and germ cells. Cultured cell lines, including those derived from any of the above, may also be used. In another aspect of the invention, however, partially and fully differentiated cells may also be used if desired. By way of a non-limiting example, the use of differentiated cells is preferred if the gene sequence to be underexpressed is normally only expressed in said differentiated cells. For the transduction of different cell types, the vectors may be appropriately packaged via the use of pseudotype and amphotropic packaging systems known in the art.

The ability to transduce a variety of cell types provides another advantage of the present invention, wherein the over and under expression of a gene sequence in a variety of (heterologous) cell types may be used to provide added information and thus enhance assignment of gene function. This enhancement is due in part to the differences in endogenous gene expression in different cell types. Thus the full range of functionalities for a gene sequence may be better elucidated by evaluating its over and under expression in a variety of cell types.

The expression of a gene sequence of interest in a heterologous cell based upon one of more functions as identified by the present invention also provides a means to alter the phenotype of said cell. As a non-limiting example, over expression of a gene sequence may result in the elevated expression of a cell surface marker in cells normally expressing the sequence. In a heterologous cell that normally does not express the sequence, expression of the sequence therein may result in expression of the cell marker on the surface of the heterologous cells, thus providing a novel way to identify and/or target those heterologous cells.

In one preferred embodiment of the invention, the above vectors for over and under expressing a gene sequence are integrated into the cellular genome as part of the transduction process.

In yet another aspect of the invention, the detected changes in expression of cellular factors from over and under expression of a sequence can be compared to provide additional information on the functionality of the gene sequence under study. In FIG. 1, for example, the overexpression (O) of unidentified sequence 2 ("Seq 2") is shown as increasing the expression of "structural protein 1". But the underexpression (U) of Seq 2 is shown as having a very minor effect on "structural protein 1" expression compared to the control cells (Con). As such, the relationship between Seq 2 and structural protein 1 may be one where Seq 2 functions to activate or otherwise induce expression of structural protein 1 while the underexpression of Seq 2 has minimal effects on the background expression of structural protein 1.

Similarly, the functional role of the product encoded by a sequence may be analyzed by reviewing what cellular factors are similarly affected. In FIG. 1, for example, over and under expression of sequence 1 ("Seq 1") affects the expression of "transcription repressor 1" and "transcription repressor 2" identically. Thus the expressed product of Seq 1 functions to regulate these two repressors in the same way. On the other hand, the over and under expression of Seq 1 has an opposite effect on "transcription factor 2" expression. This suggests that Seq 1 functions to simultaneously regulate cellular expression of the two repressors and "transcription factor 2".

Moreover, the present invention provides a means of identifying functional relationships between unidentified sequences. In FIG. 1, for example, "Seq 3 and "Seq 4" have identical effects on the expression of "oxidoreductase 1". This would indicate that the expressed products of Seq 3 and Seq 4 are functionally related to each other at least to the extent that both function in the regulation of "oxidoreductase 1" expression. Furthermore, overexpression of "Seq 2" in FIG. 1 is shown as increasing the expression of "Seq 3" (see Seq 2's O, U and C columns for row Seq 3).

The results in FIG. 1 also illustrate other functionalities of a gene sequence. For example, "Seq 4" is shown as autoregulating its own expression when its own level of expression is analyzed. Overexpression of Seq 4 does not result in as much Seq 4 RNA expression as compared to when Seq 1, 2 or 3 are overexpressed (compare the four rows for Seq 1, 2, 3 and 4 against the identical Seq columns). This would exemplify situations where the overexpression of Seq 4 results in feedback inhibition of endogenous Seq 4 expression. Similarly, underexpression of Seq 4 does not eliminate Seq 4 expression because of feedback activation of endogenous Seq 4 expression.

The detected changes in expression of cellular factors can also be combined to provide additional information on functional relationships. As a non-limiting example, subtractive hybridization can be used quantitatively to determine the difference in the expressed RNAs between cells overexpressing and underexpressing a gene sequence. For example, the total expressed RNA from a first group of cells overexpressing a gene sequence can be used to generate cDNA for subtractive hybridization against the total expressed RNA from a second group of cells underexpressing the gene sequence. If the amount of a particular RNA is higher in the cells of the first group than the second group, there will be an excess of cDNA corresponding to that particular RNA left as single stranded molecules after hybridization. This cDNA can then be isolated and detected. The subtractive hybridization is preferably also performed using cells underexpressing a gene sequence as the first group and cells overexpressing the sequence as the second group. The results of such subtractive hybridization is shown in FIG. 1, where (if applicable) there are two numbers for each unidentified sequence "Seq" under the "C" column. The first number refers to subtractive hybridization using cDNA from the overexpressing group (0) and the second number refers to using cDNA from the underexpressing group.

Additionally, subtractive hybridization can be also used to compare the expressed RNAs between control cells and those either over or under expressing a particular gene sequence. Thus RNAs expressed in control cells can be "subtracted" from RNAs expressed in cells over or under expressing a gene sequence to provide additional information on the function of said gene sequence. This approach may also be advantageous for the cloning of RNAs that are differentially expressed between normal cells and those over or under expressing a particular gene sequence.

The results in FIG. 1 can also be modified by placing the cells under different culture conditions. By way of non-limiting examples, the cells can be placed under active growth and/or proliferation conditions, quiescent conditions, temperature shifted conditions, and in the presence of a ligand conditions before the RNA is prepared. The use of such conditions provides additional information for determining one or more functionalities of a gene sequence of interest.

In another aspect of the invention, one or more additional gene sequences are simultaneously over or under expressed in combination with the over or under expression of a first gene of interest. As a non-limiting example, and based on FIG. 1, cells transduced with a vector that overexpresses Seq 1 may instead be separately transduced with vectors that simultaneously either over or under expresses another sequence (e.g. "Seq 5"). Similarly, cells transduced with a vector that underexpresses Seq 1 may instead be separately transduced with vectors that simultaneously either over or under expresses "Seq 5". Such simultaneous over or under expression techniques provides additional information to identify or confirm the function(s) as well as functional relationship(s) of any gene sequence.

In another embodiment of this simultaneous approach, at least a third vector may be used to simultaneously over or under express the one or more additional gene sequences. Of course the vector would be one that is compatible with the vector(s) used to over or under express the first gene sequence. In yet another embodiment of this simultaneous approach, the first gene sequence may be closely related to the one or more additional gene sequences being simultaneously over or underexpresses. As a non-limiting example, the first gene sequence may be a wildtype sequence, the cell used may be homozygous for a misfunctioning mutant of the sequence, and the additional gene sequence to be expressed is an antisense version of the endogenous sequence encoding the misfunctioning mutant. By simultaneously expressing the wildtype sequence and underexpressing the misfunctioning mutant sequence by use of the additional gene sequence, the wildtype activity of the first gene sequence may be restored to the cell.

In another embodiment of the simultaneous approach, the additional gene sequence may encode an oncogene or a tumor suppressor gene.

An another aspect of the invention is the use of a high throughput system for the practice of the present invention. In one embodiment of this aspect, the system maybe optionally computerized or robot implemented, and may also include the use of the arrays described above. In one embodiment of this approach, the invention provides libraries of gene sequences, over and under expression vectors containing them, cells transduced with said vectors, and the effects on cellular factors by analysis of said cells. Preferably, the libraries of gene sequences are present in a multiplicity of compartments, each of which contains one gene sequence. In a particularly preferred format, the compartments are in a multi-well vessel, such as, but without limiting the invention, a multi-well plate. Such a multi-well vessels may be considered arrays containing all or part of gene sequence libraries, and the organization of sequences present in such arrays may be maintained throughout the practice of the invention, up to and including the analysis on the effects on cellular factors. Of particular advantage for the practice of the invention is the use of vectors containing only one gene sequence to transduce cells in each compartment.

In another aspect of the invention, separate arrays may be used for over and under expressing a gene sequence of interest. But the effects on cellular factors contained in such separate arrays is preferably combined to provide greater ease of analysis. As a non-limiting example, and once the effects of over and under expression of a gene sequence are determined for each sequence of a library, the information can be combined prior to further analysis of the results. For example, FIG. 1 shows the combination of the effects on a large number of cellular factors (see left column) of over (see columns "O") and under (see columns "U") expression for sequences 1-4 of a library (see top row). The actual effects on cellular function can also be combined by means such as the "subtractive hybridization" discussed above and then simultaneously analyzed with the over and under expression data (see for example columns "C" in FIG. 1).

In an additional approach for the practice of the invention, the effects of over and under expression on cellular factors is performed on micro or macro arrays capable of being machine implemented. Such machines are preferably capable of being partially or completely automated to harvest cells over or under expressing a gene sequence to determine the effect(s) on cellular factors. In a non-limiting example for analyzing the effect on gene expression, a "gene chip" containing sequences encoding cellular factors is used to determine which of these factors is affected by over or under expressing a particular gene sequence. Thus RNAs, or cDNAs corresponding thereto, may be isolated from the cells, labeled, and hybridized against the sequences on said chip. The results of such hybridization can be compared to that seen with control cells to determine the effect on each cellular factor encoding sequence present on the chip. Of course a multiplicity of chips may be used to permit analysis of the large number of cellular factors known, as well as permit the analysis of each unidentified sequence against other unidentified sequences. Additionally, duplicates of the same chip are used for analysis of cells either over or under expressing a particular gene sequence.

Prior to analysis, the libraries of transduced cells, which over and under express a variety of sequences, may be subjected to further treatment or changing conditions. In addition to the simultaneous over or under expression of additional sequences described herein, the cells may be subjected to the presence of various factors and cultured under a variety of growth conditions. As a non-limiting example, the cells may be exposed to one or more ligands to induce a variety of effects. Alternatively, the cells may be analyzed over time or transplanted into an in vivo context to permit the identification of additional effects on cellular factors.

In additional embodiments of the invention, the analysis of effects on cellular factors may be conducted by the use of any assay. The following is provided as additional non-limiting examples of the practice of the invention. Of course these examples may be conducted by partially or completely automated means.

In a first non-limiting example, cells over or under expressing a gene sequence may be analyzed for the effects on protein levels of cellular factors. As such, a sample of the cells may be used in western blot analysis using antibodies specific for various cellular factors. Alternatively, the analysis may be conducted by other means, such as any quantitative immunoassay. Such an analysis may be done in concert with the gene expression analysis described herein to provide a more complete picture of effects on cellular factors since changes in RNA expression levels may not always be closely correlated with changes in the levels of the protein encoded by said RNA. Moreover, this approach can follow the gene expression analysis by using only antibodies directed to proteins encoded by RNAs which have been observed to change in expression.

In a second non-limiting example, cells over or under expressing a gene sequence may be analyzed for the effects on protein activity. This may be of particular interest for gene sequences encoding an activator or inhibitor of another protein or enzyme. A sample of the cells may be used in enzymatic or other protein assays to detect changes in activity. For instance, the over expression of an activator of a particular kinase would increase the detectable activity of said kinase in an appropriate assay. This effect may or may not be independent of any changes in the gene expression or protein levels of the kinase.

In a third non-limiting example, the effect on protein phosphorylation may be analyzed in cells over or under expressing a gene sequence. The cells over or under expressing a gene sequence may be grown such that phosphorylated proteins are radiolabeled via the phosphorus group. Samples from such cells can then be analyzed by two-dimensional gels or appropriate immunoassays (such as with antibodies specific for known phosphoproteins) to detect changes in protein phosphorylation.

In a fourth non-limiting example, cells over or under expressing a gene sequence can be analyzed for the effects on cellular factors that are not gene products. For instance, the effect on intracellular concentrations of various small molecules (such as calcium, sodium, and chloride ions; intermediates in various enzymatic cycles; lipids; etc.) may be analyzed. In other instances, the production and expression of various cellular factors on the cell surface, such as lipids or sugars, are detected.

The present invention also provides an advantageous means of isolating the product encoded by a gene sequence, which can be simply accomplished by harvesting cells over expressing said sequence and purifying said product.

The present invention further provides advantages in that no functionality need be known for a sequence being over and under expressed. As such, the time and cost necessary for bioinformatics may be optionally removed, although the inclusion of bioinformatics information in the practice of the present invention would increase the likelihood of accurately assigning functionalities to a gene sequence.

Moreover, the invention provides the ability to relate the functionality of one unidentified gene sequence to another. The invention further permits the combination of this ability, with the advantageous capability of identifying functional relatedness between unidentified and known sequences, to provide the determination of a family of functionally related gene sequences. The relatedness of individual family members may be expressed as a map based on functional relationships, which would otherwise not be recognized without extensive research.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method of identifying a function of a polypeptide-encoding sequence of interest endogenously expressed by a cell type using high throughput detection, comprising:
   a) providing a first pseudotyped lentiviral vector, comprising at least a part of the polypeptide-encoding sequence of interest, wherein the polypeptide-encoding sequence of interest is a known or unidentified gene sequence, and wherein the first lentiviral vector is designed to express little or no vector borne sequence other than the at least a part of the polypeptide-encoding sequence of interest, and
   b) providing a second pseudotyped lentiviral vector, comprising an inhibitory or termination sequence, wherein the inhibitory or termination sequence can inhibit, terminate, or underexpress the endogenously expressed polypeptide-encoding sequence of interest, and wherein the second lentiviral vector is designed to express little or no vector borne sequence other than the inhibitory or termination sequence,
   c) providing a first and a second population of the cell type, and transducing the first lentiviral vector in the first cell population and transducing the second lentiviral vector in the second cell population;
   d) expressing all or part of the polypeptide-encoding sequence of interest in the first cell population and inhibiting, terminating, or underexpressing the polypeptide-encoding sequence of interest in the second cell population;
   e) high throughput detecting at least one change in one or more endogenous cellular factors in the first and second cell populations by comparing the effect on the cell of expression of the polypeptide-encoding sequence of interest with the effect on the cell of inhibition, or termination, or underexpression of the polypeptide-encoding sequence of interest; and
   f) identifying a function of the polypeptide-encoding sequence of interest based on the detected and compared effect on the cell of expression and inhibition, or termination, or underexpression of the polypeptide-encoding sequence of interest on one or more cellular factors.

2. The method of claim 1, wherein the at least one change is an increase and/or decrease in the expression of the endogenous cellular factor.

3. The method of claim 1, wherein the at least one change is in a post-translational modification of the endogenous cellular factor.

4. The method of claim 3, wherein the post-translational modification comprises a phosphorylation or glycosylation of the cellular factor.

5. The method of claim 1, wherein the at least one change is in an activity of the cellular factor.

6. The method of claim 1, wherein the first and/or second pseudotyped lentiviral vector is a conditionally replicating pseudotyped lentiviral vector.

7. The method of claim 1, wherein the inhibitory or termination sequence comprises all or part of the polypeptide-encoding sequence of interest in an antisense orientation.

8. The method of claim 1, wherein the inhibitory or termination sequence comprises a sequence encoding for one or more ribozymes against the polypeptide-encoding sequence of interest.

9. The method of claim 1, wherein the inhibitory or termination sequence comprises a sequence encoding a double stranded RNA against the polypeptide-encoding sequence of interest.

10. The method of claim 1, wherein the cell type is a primary cell.

11. The method of claim 1, wherein the polypeptide-encoding sequence of interest encodes a product which modulates expression of the one or more cellular factors by binding to nucleic acids encoding, or regulating the expression of, the one or more cellular factors.

12. The method of claim 11, wherein the polypeptide-encoding sequence of interest encodes a transcriptional activator.

13. The method of claim 11, wherein the polypeptide-encoding sequence of interest encodes a transcriptional repressor.

14. The method of claim 1, wherein the polypeptide-encoding sequence of interest is a human sequence.

15. The method of claim 1, wherein the cell type is a human, a plant or a microorganism cell type.

16. A method of altering the expression of one or more cellular factors in a cell comprising expressing or inhibiting, terminating, or underexpressing a gene sequence for which a function was identified by the method of claim 1.

17. A method of altering the phenotype of a cell comprising expressing or inhibiting, terminating, or underexpressing a gene sequence for which a function was identified by the method of claim 1.

18. A method of identifying a function of a gene sequence of interest in a cell heterologous to the cellular source of the gene sequence of interest using high throughput detection, comprising:
   a) providing a pseudotyped lentiviral vector, comprising at least a part of the gene sequence of interest, wherein the gene sequence of interest is a known gene sequence, and wherein the pseudotyped lentiviral vector is designed to express little or no vector borne sequence other than the at least a part of the gene sequence of interest, and
   wherein the expression is relative to the level of expression of the gene sequence in a cell from which the gene sequence was derived, (b) providing a population of the cell, and transducing the lentiviral vector in the cell population;

(c) expressing all or part of the gene sequence of interest in the cell population;

(d) high throughput detecting at least one change in one or more cellular factors in the cell population when compared to the expression of the gene sequence of interest in the cell from which the gene sequence was derived; and (e) identifying a function of the gene sequence of interest based on the detected and compared effect on the cell of expression of the gene sequence of interest and expression of the gene sequence of interest in the cell from which the gene sequence was derived, on one or more cellular factors.

19. A method of detecting, using high throughput detection, a change in one or more cellular factors in a cell due to the expression and inhibition, termination, or underexpression of a gene sequence of interest in the cell, comprising:

a) providing a first pseudotyped lentiviral vector, comprising at least a part of the gene sequence of interest, wherein the gene sequence of interest is a known or unidentified gene sequence, and wherein the first lentiviral vector is designed to express little or no vector borne sequence other than the at least a part of the gene sequence of interest, and b) providing a second pseudotyped lentiviral vector, comprising an inhibitory or termination sequence, wherein the inhibitory or termination sequence can inhibit, terminate, or underexpress the gene sequence of interest, and wherein the second lentiviral vector is designed to express little or no vector borne sequence other than the inhibitory or termination sequence, c) providing a first and a second population of the cell type, and transducing the first lentiviral vector in the first cell population and transducing the second lentiviral vector in the second cell population.

d) expressing all or part of the gene sequence of interest in the first cell population and inhibiting, terminating, or underexpressing the gene sequence of interest in the second cell population; and e) high throughput detecting at least one change in one or more endogenous cellular factors in the first and second cell populations by comparing the effect on the cell of expression of the gene sequence of interest with the effect on the cell of inhibition, termination, or underexpression of the gene sequence of interest.

20. The method of claim 19, further comprising a step:

f) identifying a function of the gene sequence of interest based on the detected and compared effect on the cell of expression and inhibition, termination, or underexpression of the gene sequence of interest on one or more cellular factors.

21. The method of claim 20, further comprising a step:

g altering the expression of the one or more cellular factors in a third population of the cell type cell by expressing or inhibiting or terminating the expression of the gene sequence of interest for which a function was identified in step f.

22. The method of claim 20, further comprising a step:

g altering the phenotype of a third population of the cell type by expressing or inhibiting, terminating, or underexpressing the said gene sequence of interest for which a function was identified in step f.

23. The method of claim 19, wherein the cell is heterologous to the cellular source of the gene sequence of interest, and expression and underexpression or termination is relative to the level of expression of the gene sequence of interest in a cell from which the gene sequence of interest was derived.

24. The method of claim 19, wherein the cellular factor comprises a cellular gene product or a metabolite.

25. The method of claim 24, wherein the cellular gene product comprises a protein or RNA.

26. The method of claim 24, wherein the metabolite comprises a sugar or a lipid.

27. The method of claim 1, wherein inhibiting, terminating, or underexpressing the polypeptide-encoding sequence of interest is mediated by post-transcriptional gene silencing (PTGS), small interfering RNA (siRNA), RNA interference, or an antisense or a ribozyme sequence targeted against the polypeptide-encoding sequence of interest.

28. The method of claim 1, wherein the high throughput detecting comprises use of computerized or robot implemented systems.

29. The method of claim 1, wherein the high throughput detecting comprises use of libraries of pseudotyped lentiviral vectors and cells transduced by the pseudotyped lentiviral vectors.

30. The method of claim 1, wherein the high throughput detecting comprises use of libraries of pseudotyped lentiviral vectors and cells transduced by the pseudotyped lentiviral vectors in a multiplicity of compartments.

31. The method of claim 1, wherein the high throughput detecting comprises use of machine implemented microarray or macroarray technology.

32. The method of claim 18, wherein the high throughput detecting comprises use of computerized or robot implemented systems.

33. The method of claim 19, wherein the high throughput detecting comprises use of computerized or robot implemented systems.

34. The method of claim 1, wherein the inhibitory or termination sequence comprises a sequence encoding a short interfering (si) RNA.

35. The method of claim 1, wherein the inhibitory or termination sequence comprises an antisense sequence ligated to a co-localization sequence.

* * * * *